US005756436A

United States Patent [19]
Royce et al.

[11] Patent Number: 5,756,436
[45] Date of Patent: May 26, 1998

[54] CONDITIONING SHAMPOO COMPOSITIONS CONTAINING SELECT CATIONIC CONDITIONING POLYMERS

[75] Inventors: Douglas Allan Royce, Auroa, Ind.; Susan Marie Guskey, Montgomery, Ohio; Everett Junior Inman, Cincinnati, Ohio; Timothy Woodrow Coffindaffer, Loveland, Ohio

[73] Assignee: The Procter & Gamble Company, Cincinnati, Ohio

[21] Appl. No.: 622,972

[22] Filed: Mar. 27, 1996

[51] Int. Cl.$^6$ .............. C11D 1/12; C11D 1/65; C11D 9/36; C11D 3/37

[52] U.S. Cl. .............. 510/122; 510/123; 510/127; 510/156; 510/476; 510/501; 510/504; 510/126

[58] Field of Search ............... 510/122, 123, 510/127, 156, 476, 501, 504, 126

[56] References Cited

U.S. PATENT DOCUMENTS

| | | | |
|---|---|---|---|
| 2,826,551 | 3/1958 | Green | 252/89 |
| 3,149,178 | 9/1964 | Hamilton | 260/683.9 |
| 3,382,291 | 5/1968 | Brennan | 260/683.15 |
| 3,725,498 | 4/1973 | Brennan | 260/683.15 B |
| 3,964,500 | 6/1976 | Drakoff | 132/7 |
| 4,167,486 | 9/1979 | Rowe | 252/56 R |
| 4,175,046 | 11/1979 | Coant et al. | 252/56 S |
| 4,304,678 | 12/1981 | Schick et al. | 252/56 R |
| 4,364,837 | 12/1982 | Pader | 252/173 |
| 4,524,007 | 6/1985 | Chibnik | 252/56 R |
| 4,555,353 | 11/1985 | Horodysky et al. | 252/49.6 |
| 4,587,026 | 5/1986 | Horodysky | 252/47.5 |
| 4,657,690 | 4/1987 | Grollier et al. | 252/90 |
| 4,664,835 | 5/1987 | Grollier et al. | 252/90 |
| 4,741,855 | 5/1988 | Grote et al. | 252/142 |
| 4,806,345 | 2/1989 | Bhattacharyya | 424/70 |
| 4,834,893 | 5/1989 | Doner et al. | 252/32.7 E |
| 4,967,029 | 10/1990 | Wu | 585/12 |
| 5,011,681 | 4/1991 | Ciotti et al. | 424/81 |
| 5,019,282 | 5/1991 | Farng et al. | 252/32.7 E |
| 5,034,218 | 7/1991 | Duvel | 424/70 |
| 5,085,857 | 2/1992 | Reid et al. | 424/70 |
| 5,105,038 | 4/1992 | Chen et al. | 585/10 |
| 5,221,530 | 6/1993 | Janchitraponvej et al. | 424/70 |
| 5,338,470 | 8/1994 | Hiebert et al. | 252/51.5 |
| 5,417,965 | 5/1995 | Janchitraponvej | 424/70 |
| 5,573,709 | 11/1996 | Wells | 510/122 |
| 5,589,177 | 12/1996 | Herb et al. | 424/401 |

FOREIGN PATENT DOCUMENTS

| | | | |
|---|---|---|---|
| 9462606 | 9/1994 | Australia | A61K 7/48 |
| 0 413 416 A2 | 2/1991 | European Pat. Off. | A61K 7/06 |
| 0 413 417 B1 | 2/1991 | European Pat. Off. | A61K 7/08 |
| 0521665A1 | 1/1993 | European Pat. Off. | A61K 7/06 |
| 54-129135 | 10/1979 | Japan | A61K 7/06 |
| 56-72095 | 6/1981 | Japan | C11D 3/37 |
| 1-168612 | 12/1987 | Japan | A61K 7/50 |
| 849433 | 9/1960 | United Kingdom . | |

*Primary Examiner*—Paul Lieberman
*Assistant Examiner*—Charles Boyer
*Attorney, Agent, or Firm*—David L. Suter; David K. Dabbiere; William J. Winter

[57] ABSTRACT

Disclosed are aqueous conditioning shampoo compositions which comprise an anionic detersive surfactant component; dispersed, liquid, droplets of a water insoluble, hair conditioning agent having a number average particle diameter of from about 0.01 microns to about 2000 microns; from about 0.025% to about 5% by weight of an organic, cationic, non crosslinked, deposition or conditioning polymer having a cationic charge density of from about 4 meq/gm to about 7 meq/gm and an average molecular weight of from about 1,000 to about 1 million. The cationic polymer, in combination with anionic detersive surfactant component and other essential components, provides improved deposition of the conditioning agent on hair or skin, even when the dispersed conditioning agent particles have a number average particle size of up to about 2,000 microns. The composition may be applied to skin or hair, and provides improved conditioning performance even without the use of the dispersed hair conditioning agent particles.

33 Claims, No Drawings

CONDITIONING SHAMPOO COMPOSITIONS CONTAINING SELECT CATIONIC CONDITIONING POLYMERS

FIELD OF THE INVENTION

The present invention relates to conditioning shampoo compositions with improved conditioning performance which comprise select cationic deposition polymers.

BACKGROUND OF THE INVENTION

Conditioning shampoos comprising various combinations of detersive surfactant and hair conditioning agents are known. These shampoo products typically comprise an anionic detersive surfactant in combination with a conditioning agent such as silicone, hydrocarbon oil, fatty esters, or combinations thereof. These shampoos have become more popular among consumers as a means of conveniently obtaining hair conditioning and hair cleansing performance all from a single hair care product.

Many conditioning shampoos, however, do not provide sufficient deposition of conditioning agents onto hair during the shampooing process. Without such deposition, large proportions of conditioning agent are rinsed away during the shampooing process and therefore provide little or no conditioning benefit. Without sufficient deposition of the conditioning agent on the hair, relatively high levels of conditioning agents may be needed in the shampoo composition to provide adequate hair conditioning performance. Such high levels of a conditioning agent, however, can increase raw material costs, reduce lathering, and present product stability concerns.

Obtaining good deposition of a conditioning agent onto hair is further complicated by the action of detersive surfactants in the shampoo. Detersive surfactants are designed to carry away or remove, oil, grease, dirt, and particulate matter from the hair and scalp. In doing so, the detersive surfactants can also interfere with deposition of the conditioning agent, and carry away both deposited and non deposited conditioning agent during rinsing. This further reduces deposition of the conditioning agent onto the hair after rinsing, thus further reducing hair conditioning performance.

One known method for improving deposition of a hair conditioning agent onto hair involves the use of certain cationic deposition polymers. These polymers may be synthetic, but are most typically natural cellulosic or guar polymers that have been modified with cationic substituents. The cationic charge density of such polymers, especially when used in a shampoo composition, is minimized so as to avoid incompatibility with anionic materials in the shampoo such as anionic surfactant. As such, most shampoos which contain both an anionic detersive surfactant and a cationic deposition polymer will maintain relatively low cationic charge density values for the deposition polymer in order to maintain physical stability of the shampoo composition.

It has now been found that select synthetic cationic polymers provide improved hair conditioning performance, especially wet hair conditioning, and improved deposition of dispersed hair conditioning agent particles onto hair or skin. These select polymers are especially effective at improving deposition of dispersed hair conditioning agents onto hair and skin, especially when used in combination with an anionic detersive surfactant component in a shampoo composition. These select polymers are organic, non crosslinked, cationic polymers which have a relatively high charge density of from about 4 meq/gm to about 7 meq/gm and a relatively low weight average molecular weight of from about 1,000 to about 1 million. The select cationic polymers provide improved deposition of the dispersed conditioning agent in the shampoo composition, even when the dispersed conditioning agent particles have relatively large average particle diameters of up to about 2,000 microns.

It has also been found that the shampoo compositions defined herein, which contain the highly charged cationic polymers, remain stable (e.g., maintains a smooth, flowable, liquid rheology) even though the shampoo compositions also contains an anionic detersive surfactant component.

It is therefore an object of the present invention to provide a conditioning shampoo composition for use on hair or skin with improved conditioning performance, and further to provide such a composition with improved deposition of dispersed, water insoluble, conditioning agent onto hair or skin, and further to provide such a composition with improved deposition of dispersed, water insoluble, conditioning agent particles having an average particle size of from about 0.01 microns up to about 2,000 microns. It is yet another object of the present invention to provide a conditioning shampoo composition with improved conditioning performance using a reduced concentration of hair conditioning agent. It is yet another object of the present invent to provide a stable shampoo composition which contains both an anionic detersive surfactant component and a highly charged, cationic deposition or conditioning polymer.

SUMMARY OF THE INVENTION

The present invention is directed to conditioning shampoo compositions which comprise (A) from about 5% to about 50% by weight of an anionic detersive surfactant component selected from the group consisting of anionic surfactants, amphoteric or zwitterionic surfactants having an attached group that is anionic at the pH of the composition, and combinations thereof; (B) from about 0.05% to about 20% by weight of dispersed particles of a water insoluble, conditioning agent having a number average particle diameter of from about 0.01 microns to about 2,000 microns; (C) from about 0.025% to about 5% by weight of an organic, cationic, non crosslinked, conditioning polymer having a cationic charge density of from about 4 meq/gm to about 7 meq/gm and an average molecular weight of from about 1,000 to about 1 million; and (D) from about 20% to about 94% by weight of water. The select conditioning polymers defined herein, in combination with the other essential components, provide improved deposition of the conditioning agent on hair or skin, even when the conditioning agent is in the form of dispersed particles having average particle diameters of up to about 2,000 microns.

The present invention also relates to conditioning shampoo compositions which do not necessarily comprise the hair conditioning agent particles, and which provides improved conditioning performance.

DETAILED DESCRIPTION OF THE INVENTION

The shampoo compositions of the present invention can comprise, consist of, or consist essentially of the essential elements and limitations of the invention described herein, as well any of the additional or optional ingredients, components, or limitations described herein.

All percentages, parts and ratios are based upon the total weight of the shampoo compositions of the present invention, unless otherwise specified. All such weights as they pertain to listed ingredients are based on the active level and, therefore, do not include carriers or by-products that may be included in commercially available materials, unless otherwise specified.

As used herein, the term "soluble" refers to any material that is sufficiently soluble in water to form a substantially clear solution to the naked eye at a concentration of 0.1% by weight of the material in water at 25° C. Conversely, the term "insoluble" refers to all other materials that are therefore not sufficiently soluble in water to form a substantially clear solution to the naked eye at a concentration of 0.1% by weight of the other material in water at 25° C.

As used herein, "nonvolatile" refers to any material having little or no significant vapor pressure under ambient conditions, and a boiling point under one atmosphere (atm) preferably at least about 250° C. The vapor pressure under such conditions is preferably less than about 0.2 mm Hg at 25° C. or less, more preferably less than about 0.1 mm Hg at 25° C. or less.

The shampoo compositions of the present invention, including the essential and some optional components thereof, are described in detail hereinafter.

Anionic Detersive Surfactant Component

The shampoo compositions of the present invention comprise an anionic detersive surfactant component to provide cleaning performance to the composition. The anionic detersive surfactant component in turn comprises anionic detersive surfactant, zwitterionic or amphoteric detersive surfactant which has an attached group that is anionic at the pH of the composition, or a combination thereof, preferably anionic detersive surfactant. Such surfactants should be physically and chemically compatible with the essential components described herein, or should not otherwise unduly impair product stability, aesthetics or performance.

Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally range from about 5% to about 50%, preferably from about 8% to about 30%, more preferably from about 10% to about 25%, even more preferably from about 12% to about 18%, by weight of the composition.

Preferred anionic surfactants suitable for use in the shampoo compositions are the alkyl and alkyl ether sulfates. These materials have the respective formulae $ROSO_3M$ and $RO(C_2H_4O)_xSO_3M$, wherein R is alklyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. The cation M should be selected such that the anionic detersive surfactant component is water soluble. Solubility of the surfactant will depend upon the particular anionic detersive surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Specific non limiting examples of alkyl ether sulfates which may be used in the shampoo compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula [ $R^1$—$SO_3$—M] where $R^1$ is a straight or branched chain, saturated, aliphatic hydrocarbon radical having from about 8 to about 24, preferably about 10 to about 18, carbon atoms; and M is a cation described hereinbefore. Non limiting examples of such detersive surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. No. 2,486,921; U.S. Pat. No. 2,486,922; and U.S. Pat. No. 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxyalkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxyalkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the shampoo compositions are the beta-alkyloxy alkane sulfonates. These surfactants conform to the formula

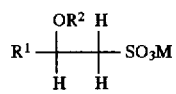

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants for use in the shampoo composition herein include those which are known for use in hair care or other personal care cleansing composition, and which contain a group that is anionic at the pH of the shampoo composition. Concentration of such amphoteric detersive surfactants preferably ranges from about 0.5 % to about 20%, preferably from about 1% to about 10%, by weight of the composition. Non limiting examples of suitable zwitterionic or amphoteric surfactants are described in U.S. Pat. Nos. 5,104,646 (Bolich Jr. et al.), U.S. Pat. No. 5,106,609 (Bolich Jr. et al.), which descriptions are incorporated herein by reference.

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate.

Zwitterionic detersive surfactants suitable for use in the shampoo composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The shampoo compositions of the present invention may further comprise additional surfactants for use in combination with the anionic detersive surfactant component described hereinbefore. Suitable optional surfactants include nonionic surfactants, cationic surfactants, and combinations thereof. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional surfactants in the shampoo composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the shampoo compositions are described in *McCutcheon's, Emulsifiers and Detergents*, 1989 *Annual*, published by M. C. Publishing Co., and U.S. Pat. No. 3,929,678, U.S. Pat. No. 2,658,072; U.S. Pat. No. 2,438,091; U.S. Pat. No. 2,528,378, which descriptions are incorporated herein by reference.

Conditioning Agent

The shampoo compositions of the present invention comprise a hair or skin conditioning agent which is a water insoluble, water dispersible, non volatile, liquid that forms discreet, emulsified, liquid particles in the surfactant matrix described hereinbefore. The conditioning agent should be physically and chemically compatible with the essential components of the composition, or should not otherwise unduly impair product stability, aesthetics or performance.

Suitable conditioning agents for use in the shampoo composition are those conditioners characterized generally as hydrocarbon oils, silicones, or combinations thereof, or those conditioners which otherwise form liquid, dispersed, particles in the aqueous surfactant matrix herein. The concentration of the conditioning agent in the shampoo composition should be sufficient to provide the desired conditioning benefits. Such concentrations can vary with the conditioning agent selected, the conditioning performance desired, the average size of the conditioning agent particles, location of the intended deposition (e.g. skin or hair), the type and concentration of other components, and other factors well known in the art.

The dispersed, conditioning agent, particles have a number average particle diameter of from about 0.01 microns to about 2,000 microns. For small particle application to hair, the number average particle diameters range from about 0.01 microns to about 4 microns, preferably from about 0.01 to about 2 microns, more preferably from about 0.01 microns to about 0.5 microns. For larger particle application to hair, the number average particle diameters range from about 4 microns to about 50 microns, preferably from about 6 microns to about 30 microns, more preferably from about 9 microns to about 20 microns, even more preferably from about 12 to about 18 microns. For application to skin, the number average particle diameters range from about 30 microns to about 2,000 microns, preferably from about 50 microns to about 1,500 microns, even more preferably from about 60 microns to about 1,000 microns.

It has been found that the select synthetic polymers described hereinafter provide improved deposition of the hair conditioning agent particles, provided that such particles are primarily in the form of dispersed, emulsified, water insoluble, droplets throughout the shampoo composition. The select polymers do not, however, readily improve deposition of other hair conditioning agents when such other agents are solubilized into the surfactant micelles of the shampoo composition rather than dispersed throughout the composition as discreet, water insoluble, droplets. Such other hair conditioning agents, however, may be added to the shampoo composition as optional materials.

Hydrocarbon oils suitable for use as the hair conditioning agent herein include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. The concentration of such hydrocarbon oils in the shampoo composition range from about 0.05% to about 20%, preferably from about 0.08% to about 1.5%, more preferably from about 0.1% to about 1%, by weight of the shampoo composition.

A) Silicone Conditioning Agent

The conditioning agent of the shampoo composition of the present invention is preferably an insoluble silicone conditioning agent, more preferably a non volatile silicone conditioning agent. Concentration of such silicone conditioning agent should be sufficient to provide the hair or skin with the desired conditioning benefit. Such concentrations range from about 0.01% to about 20%, preferably from about 0.1% to about 8%, more preferably from about 0.1% to about 5%, most preferably from about 0.2% to about 3%, by weight of the shampoo composition. Non limiting examples of suitable silicone hair conditioning agents, and optional suspending agents for the silicone, are described in U.S. Reissue Pat. No. 34,584 (Grote et al.), U.S. Pat. Nos. 5,104,646 (Bolich Jr. et al.), U.S. Patent 5,106,609 (Bolich Jr. et al.), which descriptions are incorporated herein by reference The optional silicone hair conditioning agents are also insoluble in the shampoo composition of the present invention, and forms the requisite dispersion of water insoluble, emulsified, liquid particles or droplets. The droplets are typically and preferably suspended with an optional suspending agent described hereinafter. The silicone hair conditioning agent particles will comprise a silicone fluid hair conditioning agent such as a silicone fluid and can also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The silicone hair conditioning agent particles may comprise volatile silicone, nonvolatile silicone, or combinations thereof. Typically, if volatile silicones are present, it will be incidental to their use as a solvent or carrier for commercially available forms of nonvolatile silicone materials ingredients, such as silicone gums and resins.

The silicone hair conditioning agents for use in the shampoo compositions preferably have a viscosity of from about 20 to about 2,000,000 centistokes, more preferably from about 1,000 to about 1,800,000 centistokes, even more preferably from about 50,000 to about 1,500,000 centistokes, most preferably from about 100,000 to about 1,500,000 centistokes, as measured at 25° C.

Silicone fluids include silicone oils which are flowable silicone materials having a a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Silicone oils include polyalkyl or polyaryl siloxanes which conform to the following formula (I)

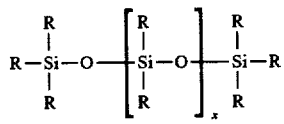

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair.

The two R groups on the silicon atom of each monomeric silicone unit may represent the same or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl -3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition hereof.

Suitable alkylamino substituted silicones include those which conform to the following structure (II)

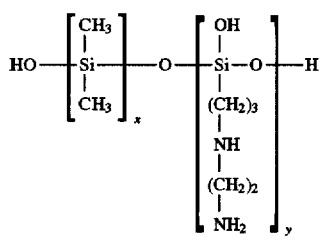

wherein x and y are integers. This polymer is also known as "amodimethicone".

Suitable cationic silicone fluids include those which conform to the formula (III) $(R_1)_aG_{3-a}$—Si—$(—OSiG_2)_n$—$(—OSiG_b(R_1)_{2-b})_m$—O—$SiG_{3-a}(R_1)_a$, wherein G is selected from the group consisting of hydrogen, phenyl, hydroxy, $C_1$-$C_8$ alkyl and preferably methyl; a is 0 or an integer having a value from 1 to 3, preferably 0; b is 0 or 1, preferably 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical conforming to the formula $CqH_{2q}L$ in which q is an integer having a value of from 2 to 8 and L is selected from the following groups:

—$N(R_2)CH_2$—$CH_2$—$N(R_2)_2$

—$N(R_2)_2$

—$N(R_2)_3A^-$

—$N(R_2)CH_2$—$CH_2$—$NR_2H_2A^-$ in which $R_2$ is selected from the group consisting of hydrogen, phenyl, benzyl, a saturated hydrocarbon radical, preferably an alkyl radical containing from 1 to 20 carbon atoms, and $A^-$ is a halide ion.

An especially preferred cationic silicone corresponding to formula (III) is the polymer known as "trimethylsilylamodimethicone", of formula (IV):

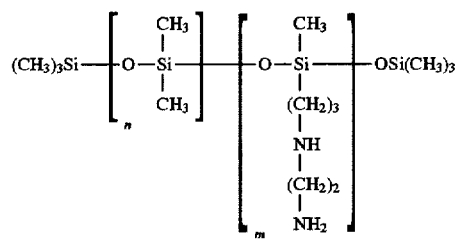

Other silicone cationic polymers which can be used in the shampoo compositions are represented by the formula (V):

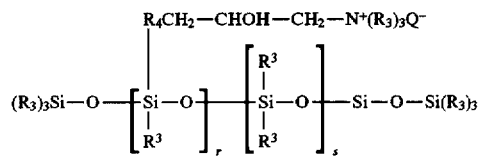

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$-$C_{18}$ alkylene radical or a $C_1$-$C_{18}$, and more preferably $C_1$-$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCARE SILICONE ALE 56."

Other optional silicone fluids are the insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Another category of nonvolatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (1) above, as well as cyclic polysiloxanes such as those represented by Formula (VI) below:

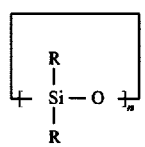

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm$^2$, typically at least about 27 dynes/cm$^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1$NHR$^2$NH2 where each $R^1$ and $R^2$ independently is a $C_1$–$C_3$ alkyl, alkenyl, and/or alkoxy. High refractive index polysiloxanes are available from Dow Corning Corporation (Midland, Michigan, U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably 30 dynes/cm$^2$ or less, more preferably about 28 dynes/cm$^2$ or less most preferably about 25 dynes/cm$^2$ or less. Typically the surface tension will be in the range of from about 15 to about 30, more typically from about 18 to about 28, and most generally from about 20 to about 25 dynes/cm$^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus is contemplated that ratios significantly above 1000:1 maybe used.

References disclosing examples of some suitable silicone fluids for use in the shampoo compositions include U.S. Pat. No. 2,826,551, U.S. Pat. No. 3,964,500, U.S. Pat. No. 4,364,837, British Patent 849,433, and *Silicon Compounds*, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

B) Suspending Agent

The shampoo compositions of the present invention may further comprise a suspending agent at concentrations effective for suspending the optional silicone hair conditioning agent, or other water-insoluble, dispersed material in the shampoo compositions. Such concentrations range from about 0.1% to about 10%, preferably from about 0.3% to about 5.0%, by weight of the shampoo compositions.

Suitable suspending agents include crystalline suspending agents that can be categorized as acyl derivatives, long chain amine oxides, or combinations thereof, concentrations of which range from about 0.1% to about 5.0%, preferably from about 0.5% to about 3.0%, by weight of the shampoo compositions. When used in the shampoo compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., U.S.A.).

Examples of suitable long chain amine oxides for use as suspending agents include alkyl ($C_{16}$–$C_{22}$) dimethyl amine oxides, e.g., stearyl dimethyl amine oxide.

Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Synthetic Cationic Polymer

The shampoo compositions of the present invention comprise certain cationic deposition or conditioning polymers having a selectively high cationic charge density and a low molecular weight. These cationic polymers, in combination with the anionic surfactant component and other essential components herein, form a stable shampoo composition that provides improved conditioning performance, and also provides improved deposition of the dispersed, hair conditioning agent particles (described hereinbefore) onto hair.

The cationic polymers suitable for use in the shampoo composition herein are water soluble or dispersible, non crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymer in the shampoo composition ranges about 0.025% to about 5%, preferably from about 0.1% to about 3%, more preferably from about 0.2% to about 1%, by weight of the composition.

The cationic polymers for use in the shampoo composition must be non crosslinked, and comprise from about 50% to about 100%, preferably from about 70% to about 100%, most preferably about 100% (mole percent), of a cationic substituted monomer, wherein the cationic substituent is a quaternary ammonium or protonated amino group. Suitable monomers are the cationic substituted dialkylaminoalkyl acrylamides, dialkylaminoalkyl methacrylamides, dialkylaminoalkyl acrylates, dialkylaminoalkyl methacrylates, and combinations thereof, preferably dialkylaminoalkyl acrylamides, dialkylaminoalkyl methacrylamides, and combinations thereof. The cationic substituents on each of the selected monomers are quaternary ammonium or protonated amino groups (acid addition salts).

The cationic polymer may further comprise from zero to 50%, preferably less than 30%, most preferably zero percent (molar percent), of a nonionic monomer having a carbon—carbon double bond that is polymerizable with the essential cationic-substituted monomers described hereinabove. Non limiting examples of such nonionic monomers are ethylene, propylene, butylene, isobutylene, eicosene, maleic anhydride, acrylamide, methacrylamide, maleic acid, acrolein, cyclohexene, ethyl vinyl ether, methyl vinyl ether, and combinations thereof.

Preferred cationic substituted monomers are the cationic substituted dialkylaminoalkyl acrylamides, dialkylaminoalkyl methacrylamides, and combinations thereof. These preferred monomers conform the to the formula

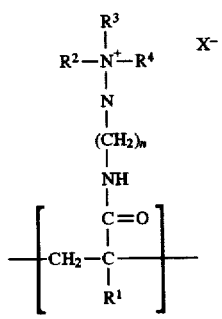

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups.

The anionic counterion (X) in association with the cationic conditioning polymers may be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfate and methylsulfate.

A non limiting example of a commercially available cationic conditioning or deposition polymer for use in the shampoo compositions is polymethyacrylamidopropyl trimonium chloride, available under the trade name Polycare 133, from Rhone-Poulenc, Cranberry, N.J., U.S.A.

Water

The shampoo compositions of the present invention are aqueous systems which comprise from about 20% to about 94%, preferably from about 50% to about 90%, more preferably from about 60% to about 85%, water by weight of the composition.

Optional Components

The shampoo compositions of the present invention may further comprise one or more optional components known for use in hair or personal care products, provided that the optional components are physically and chemically compatible with the essential component described herein, or do not otherwise unduly impair product stability, aesthetics or performance. Concentrations of such optional components typically and individually range from about 0.001% to about 10% by weight of the shampoo compositions.

Non limiting examples of optional components for use in the shampoo composition include anti static agents, conditioning agents, dyes, organic solvents or diluents, pearlescent aids, foam boosters, additional surfactants or cosurfactants (nonionic, cationic), pediculocides, pH adjusting agents, perfumes, preservatives, proteins, skin active agents, styling polymers, sunscreens, vitamins, and viscosity adjusting agents.

Method of Use

The shampoo compositions of the present invention are used in a conventional manner for cleansing and conditioning hair or skin. An effective amount of the composition for cleansing and conditioning the hair or skin is applied to the hair or skin, that has preferably been wetted with water, and then rinsed off. Such effective amounts generally range from about 1 gm to about 50 gm, preferably from about 1 gm to about 20 gm. Application to the hair typically includes working the composition through the hair such that most or all of the hair is contacted with the composition.

This method for cleansing and conditioning the hair or skin comprises the steps of: a) wetting the hair or skin with water, b) applying an effective amount of the shampoo composition to the hair or skin, and c) rinsing the applied areas of skin or hair with water. These steps can be repeated as many times as desired to achieve the desired cleansing and conditioning benefit

Examples

The shampoo compositions illustrated in Examples I–XV are specific embodiments of the shampoo compositions of the present invention, but are not intended to be limiting thereof. Other modifications can be undertaken by the skilled artisan without departing from the spirit and scope of this invention. These exemplified embodiments of the shampoo compositions of the present invention provide cleansing of hair and improved hair conditioning performance.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

| Component | Example Number | | | | |
|---|---|---|---|---|---|
| | I | II | III | IV | V |
| Ammonium Laureth-3 Sulfate | 10.00 | 10.00 | 10.00 | 10.00 | 10.00 |
| Ammonium Lauryl Sulfate | 6.00 | 6.00 | 6.00 | 6.00 | 6.00 |
| Polycare 133(2) | 0.50 | 0.25 | 0.75 | 0.50 | 0.50 |
| Cocamide MEA | 0.80 | 0.80 | 0.80 | 0.80 | 0.80 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| Ethylene Glycol Distearate | 1.50 | 1.50 | 1.50 | 1.50 | 1.50 |
| Dimethicone(1) | 1.00 | 1.00 | 1.00 | 0.50 | 1.50 |
| Perfume Solution | 0.60 | 0.60 | 0.60 | 0.60 | 0.60 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| Component | Example Number | | | | |
|---|---|---|---|---|---|
| | VI | VII | VIII | IX | X |
| Ammonium Laureth-3 Sulfate | 10.00 | 10.00 | 12.00 | 10.00 | 12.00 |
| Ammonium Lauryl Sulfate | 6.00 | 6.00 | 4.00 | 6.00 | 4.00 |
| Polycare 133(2) | 0.50 | 0.25 | 0.50 | 0.50 | 0.25 |
| Cocamide MEA | 0.80 | 0 | 0.68 | 0.80 | 0.68 |
| Cetyl Alcohol | 0.42 | 0.42 | 0.42 | 0 | 0.42 |
| Stearyl Alcohol | 0.18 | 0.18 | 0.18 | 0 | 0.18 |
| Ethylene Glycol Distearate | 1.50 | 1.50 | 1.50 | 1.50 | 1.50 |
| Dimethicone(1) | 0.25 | 1.00 | 1.00 | 1.00 | 1.00 |
| Perfume Solution | 0.60 | 0.60 | 0.60 | 0.60 | 0.60 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| Component | Example Number | | | | |
|---|---|---|---|---|---|
| | XI | XII | XIII | XIV | XV |
| Ammonium Laureth-3 Sulfate | 5.80 | 5.80 | 5.80 | 5.80 | 5.80 |
| Ammonium Lauryl Sulfate | 5.70 | 5.70 | 5.70 | 5.70 | 5.70 |
| Cocamidopropylbetaine | 2.50 | 2.50 | 2.50 | 2.50 | 2.50 |
| Polycare 133(2) | 0.50 | 0.25 | 0.50 | 0.75 | 1.00 |
| Cocamide MEA | 0.68 | 0.68 | 0.68 | 0.68 | 0.68 |
| Cetyl Alcohol | 0.42 | 0.42 | 0.42 | 0.42 | 0 |
| Stearyl Alcohol | 0.18 | 0.18 | 0.18 | 0.18 | 0 |
| Ethylene Glycol Distearate | 1.50 | 1.50 | 1.50 | 1.50 | 1.50 |
| Dimethicone(1) | 2.00 | 1.50 | 1.00 | 1.00 | 0.25 |
| Perfume Solution | 0.60 | 0.60 | 0.60 | 0.60 | 0.60 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

(1)Dimethicone is a 40(gum)/60(fluid) weight ratio blend of SE-76 dimethicone gum available from General Electric Silicones Division and a dimethicone fluid having a viscosity of 350 centistokes.
(2)Polycare 133 is Polymethacrylamidopropyl Trimonium Chloride, a non-crosslinked cationic polymer available from Rhone-Poulenc.

What is claimed is:

1. A conditioning shampoo composition comprising:

(A) from about 5% to about 50% by weight of an detersive surfactant component selected from the group consisting of anionic surfactants, amphoteric or zwitterionic surfactants having an attached group that is anionic at the pH of the composition, and combinations thereof;

(B) from about 0.05% to about 5% by weight of dispersed droplets of a water insoluble, hair conditioning agent having a number average droplet diameter of from about 4.0 microns to about 50 microns;

(C) from about 0.025% to about 5% by weight of an organic, cationic, non crosslinked, deposition polymer having a cationic charge density of from 4 meq/gm to about 7 meq/gm and an average molecular weight of from about 1,000 to about 500,000; and (D) from about 20% to about 94% by weight of water.

2. The shampoo composition of claim 1 wherein the composition comprises from about 8% to about 30% of alkyl sulfate, alkyl ether sulfate, or combinations thereof.

3. The shampoo composition of claim 1 wherein the hair conditioning agent is a silicone conditioning agent.

4. The shampoo composition of claim 3 wherein the silicone conditioning agent is a non volatile, polyalkylsiloxane fluid.

5. The shampoo composition of claim 4 wherein the polyalkylsiloxane fluid is polydimethylsiloxane fluid.

6. The shampoo composition of claim 1 wherein the number average droplet diameter of the hair conditioning agent particles is from about 4 microns to about 50 microns.

7. The shampoo composition of claim 6 wherein the number average droplet diameter of the hair conditioning agent particles is from about 9 to about 20 microns.

8. The shampoo composition of claim 1 wherein the cationic charge density of the cationic polymer is from 4 meq/gm to about 6 meq/gm.

9. The shampoo composition of claim 8 wherein the cationic polymer has an average molecular weight of from about 10,000 to about 500,000.

10. The shampoo composition of claim 8 wherein the cationic polymer is derived from monomer units selected from the group consisting of cationic substituted dialkylaminoalkyl acrylamides, dialkylaminoalkyl methacrylamides, dialkylaminoalkyl acrylates, dialkylaminoalkyl methacrylates, and combinations thereof.

11. The shampoo composition of claim 10 wherein the cationic polymer is derived from monomer units selected from the group consisting of cationic substituted dialkylaminoalkyl acrylamides, dialkylaminoalkyl methacrylamides, and combinations thereof.

12. The shampoo composition of claim 11 wherein the cationic polymer is derived from monomer units which conform to the formula

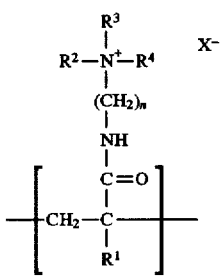

wherein $R^1$ is hydrogen, methyl or ethyl; each of $R^2$, $R^3$ and $R^4$ are independently hydrogen or a short chain alkyl having from about 1 to about 8 carbon atoms; n is an integer having a value of from about 1 to about 8; and $X^-$ is an anionic counterion.

13. The shampoo composition of claim 12 wherein $R^1$ is hydrogen or methyl; each of $R^2$, $R^3$ and $R^4$ are independently a short chain alkyl having from about 1 to about 5 carbon atoms;

and n is positive integer having a value of from about 1 to about 8, preferably from about 1 to about 4.

14. A conditioning shampoo composition comprising:
(A) from about 5% to about 50% by weight of an anionic detersive surfactant component selected from the group consisting of anionic surfactants, amphoteric or zwitterionic surfactants having an attached group that is anionic at the pH of the composition, and combinations thereof,
(B) from about 0.025% to about 5% by weight of an organic, cationic, non crosslinked, conditioning polymer having a cationic charge density of from 4 meq/gm to about 7 meq/gm and an average molecular weight of from about 1,000 to about 500,000 million; and
(C) from about 20% to about 94% by weight of water.

15. The shampoo composition of claim 14 wherein the composition comprises from about 8% to about 30% of alkyl sulfate, alkyl ether sulfate, or combinations thereof.

16. The shampoo composition of claim 14 wherein the cationic charge density of the cationic polymer is from 4 meq/gm to about 6 meq/gm.

17. The shampoo composition of claim 16 wherein the cationic polymer has an average molecular weight of from about 10,000 to about 500,000.

18. The shampoo composition of claim 14 wherein the cationic polymer is derived from monomer units selected from the group consisting of cationic substituted dialkylaminoalkyl acrylamides, dialkylaminoalkyl methacrylamides, dialkylaminoalkyl acrylates, dialkylaminoalkyl methacrylates, and combinations thereof.

19. The shampoo composition of claim 18 wherein the cationic polymer is derived from monomer units selected from the group consisting of cationic substituted dialkylaminoalkyl acrylamides, dialkylaminoalkyl methacrylamides, and combinations thereof.

20. The shampoo composition of claim 19 wherein the cationic polymer is derived from monomer units which conform to the formula

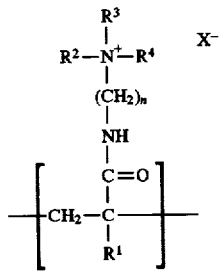

wherein $R^1$ is hydrogen, methyl or ethyl; each of $R^2$, $R^3$ and $R^4$ are independently hydrogen or a short chain alkyl having from about 1 to about 8 carbon atoms; n is an integer having a value of from about 1 to about 8; and X is an anionic counterion.

21. The shampoo composition of claim 21 wherein $R^1$ is hydrogen or methyl; each of $R^2$, $R^3$ and $R^4$ are independently a short chain alkyl having from about 1 to about 5 carbon atoms; and n is positive integer having a value of from about 1 to about 8.

22. A conditioning skin cleansing composition comprising:
(A) from about 5% to about 50% by weight of an anionic detersive surfactant component selected from the group consisting of anionic surfactants, amphoteric or zwitterionic surfactants having an attached group that is anionic at the pH of the composition, and combinations thereof;
(B) from about 0.05% to about 20% by weight of dispersed droplets of a water insoluble, conditioning agent having an number average droplets diameter of from about 4 microns to about 2,000 microns;
(C) from about 0.025% to about 5% by weight of an organic, cationic, non crosslinked, deposition polymer having a cationic charge density of from 4 meq/gm to about 7 meq/gm and an average molecular weight of from about 1,000 to about 500,000; and
(D) from about 20% to about 94% by weight of water.

23. The composition of claim 22 wherein the dispersed droplets of the conditioning agent are silicone conditioning agent, petrolatum or combinations thereof.

24. The composition of claim 23 wherein the dispersed droplets of the conditioning agent have a number average diameter of from about 50 microns to about 1,500 microns.

25. The composition of claim 24 wherein the number average droplets diameter is from about 60 microns to about 1,000 microns.

26. The shampoo composition of claim 23 wherein the conditioning agent is a silicone conditioning agent containing non volatile, insoluble, polyalkylsiloxane fluid.

27. The shampoo composition of claim 26 wherein the polyalkylsiloxane fluid is polydimethylsiloxane fluid.

28. The shampoo composition of claim 22 wherein the cationic charge density of the cationic polymer is from 4 meq/gm to about 6 meq/gm.

29. The shampoo composition of claim 28 wherein the cationic polymer has an average molecular weight of from about 10,000 to about 500,000.

30. The shampoo composition of claim 8 wherein the cationic polymer is derived from monomer units selected from the group consisting of cationic substituted dialkylaminoalkyl acrylamides, dialkylaminoalkyl methacrylamides, dialkylaminoalkyl acrylates, dialkylaminoalkyl methacrylates, and combinations thereof.

31. The shampoo composition of claim 22 wherein the cationic polymer is derived from monomer units selected from the group consisting of cationic substituted dialkylaminoalkyl acrylamides, dialkylaminoalkyl methacrylamides, and combinations thereof.

32. The shampoo composition of claim 31 wherein the cationic polymer is derived from monomer units which conform to the formula

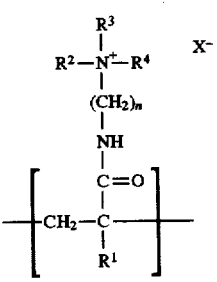

wherein $R^1$ is hydrogen, methyl or ethyl; each of $R^2$, $R^3$ and $R^4$ are independently hydrogen or a short chain alkyl having from about 1 to about 8 carbon atoms; n is an integer having a value of from about 1 to about 8; and X is an anionic counterion.

33. The shampoo composition of claim 32 wherein $R^1$ is hydrogen or methyl; each of $R^2$, $R^3$ and $R^4$ are independently a short chain alkyl having from about 1 to about 5 carbon atoms; and n is positive integer having a value of from about 1 to about 8.

* * * * *